(12) United States Patent
Richard et al.

(10) Patent No.: US 6,712,539 B2
(45) Date of Patent: Mar. 30, 2004

(54) ROLL-ON BODY POWDER DISPENSER

(75) Inventors: Wanda Richard, Ada, MI (US);
Rebecca Whipple, Grant, MI (US)

(73) Assignee: Gerber Products Company, Fremont, MI (US)

( * ) Notice: Subject to any disclaimer, the term of this patent is extended or adjusted under 35 U.S.C. 154(b) by 11 days.

(21) Appl. No.: 10/207,482

(22) Filed: Jul. 29, 2002

(65) Prior Publication Data
US 2004/0018039 A1 Jan. 29, 2004

(51) Int. Cl.[7] .............................. B43K 7/00; B43K 7/03
(52) U.S. Cl. ...................... 401/209; 401/212; 401/215; 424/69
(58) Field of Search .................. 401/208, 209–217; 424/69; 514/778

(56) References Cited

U.S. PATENT DOCUMENTS

| 4,037,977 A | | 7/1977 | Ronai |
|---|---|---|---|
| 4,272,514 A | * | 6/1981 | Spence .................. 424/69 |
| 4,342,522 A | | 8/1982 | Mackles |
| 4,368,184 A | | 1/1983 | Drucker et al. |
| 4,568,539 A | * | 2/1986 | Ashton et al. ............. 424/69 |
| 6,042,289 A | | 3/2000 | Evans et al. |
| 6,155,736 A | | 12/2000 | Evans et al. |
| 6,197,286 B1 | | 3/2001 | Scavone et al. |

OTHER PUBLICATIONS

New Gerber Wellness Baby Care Products and Services–Product Information Guide, Chapter VI Bath and Skin Care—Gerber Baby Powder, Copyright 2000 Gerber Products Company.
Package Label, Gerber Baby Powder, Soothing Protection, Pure Cornstarch, Vitamin E, with Aloe Vera, Copyright 1999.

* cited by examiner

Primary Examiner—Tuan N. Nguyen
(74) Attorney, Agent, or Firm—John W. Kung

(57) ABSTRACT

A roll-on applicator to delivery a body powder composition, especially baby powder, to areas of skin the require moisture absorption. The roll-on applicator provides superiority over shaker powders in that dust clouds and waste are minimized during application. Furthermore, the baby powder can be easily applied as the roll-on applicator glides over skin. Body powder compositions used in conjunction with the roll-on applicator contains at least an absorbent powder and a flow agent.

15 Claims, 4 Drawing Sheets

ROLL-ON BODY POWDER DISPENSER

FIELD OF THE INVENTION

The present invention relates to roll-on dispensers that can be used to apply body powder to the skin, for example baby powder. A particularly useful application of the present invention is to apply baby powder to all areas of the skin, including diaper areas of babies such that the occurrence of airborne particles during dispensing is reduced.

BACKGROUND OF THE INVENTION

Parents apply baby powders to the skin of their infants in order to absorb wetness and to prevent diaper rashes. Baby powders typically consist of fine absorbent materials such as corn starch or talc. Most baby powders that are commercially available are packaged in shaker containers. These containers have lids or caps with multiple holes to allow the powder to flow from the container when the package is shaken. The powder can be shaken onto the parent's hand or directly onto the baby's skin. During the shaking, a cloud of powder is usually created. This cloud of powder can be harmful if inhaled or ingested. Inhalation of baby powder can lead to coughing, wheezing and vomiting. Additionally, if the inhalation is severe enough, acute bronchitis and pneumonia can result. In addition to its harmful effects on health, the powder cloud also leads to waste since some of the powder is lost to the surrounding environment instead of being applied to the skin.

Roll-on applicators have been known to be used to deliver various toiletries, in particular they are used to deliver antiperspirants and deodorants. Typically these antiperspirants and deodorants are liquid formulations that can be easily and accurately applied by the rolling ball mechanism. Heretofore, these roll-on applicators have not been commonly used or marketed for the application of solid particulate materials, especially baby powders.

Thus, there is a need for product that can be used to easily dispense baby powders without creating potentially harmful powder clouds. There is also need for a product that minimizes any waste during the application of baby powder. There is also a need for a product that allows baby powder to be easily applied to the skin, the skin creases and folds which occur commonly in babies, and the diaper areas of babies. The diaper area includes the perineum, buttocks, lower abdomen and inner thighs.

SUMMARY OF THE INVENTOIN

The present invention features a roll-on dispenser that can be used to deliver a body powder, e.g., a baby powder. The body powder delivered from the dispenser can be applied to any area of the body which require excess moisture to be absorbed or removed. For example, the roll-on dispensers of the present invention are particularly suited for applying baby powder to the diaper area of an infant.

The application of the body powder is achieved through the use of a roll-on dispenser having a container, a collar, an applicator ball and a ball seat. Within the container is a body powder that is suitable for use on infants, for example corn starch or talc. When the body powder is applied to the skin, the roll-on dispenser is used in an inverted fashion which allows the body powder to flow from the container and onto the applicator ball. As the applicator ball glides across the skin, the powder dispenses in a free-flowing but controlled and loose manner. Since the powder is applied without severe agitation, for example shaking, the creation of dust clouds and occurrence of airborne particles arising from such dust clouds are minimized.

BRIEF DESCRIPTION OF THE DRAWINGS

The accompanying drawings, which are incorporated in and constitute a part of the specification, illustrate an exemplary embodiment of the present invention.

DETAILED DESCRIPTION OF THE INVENTION

Figure 1:
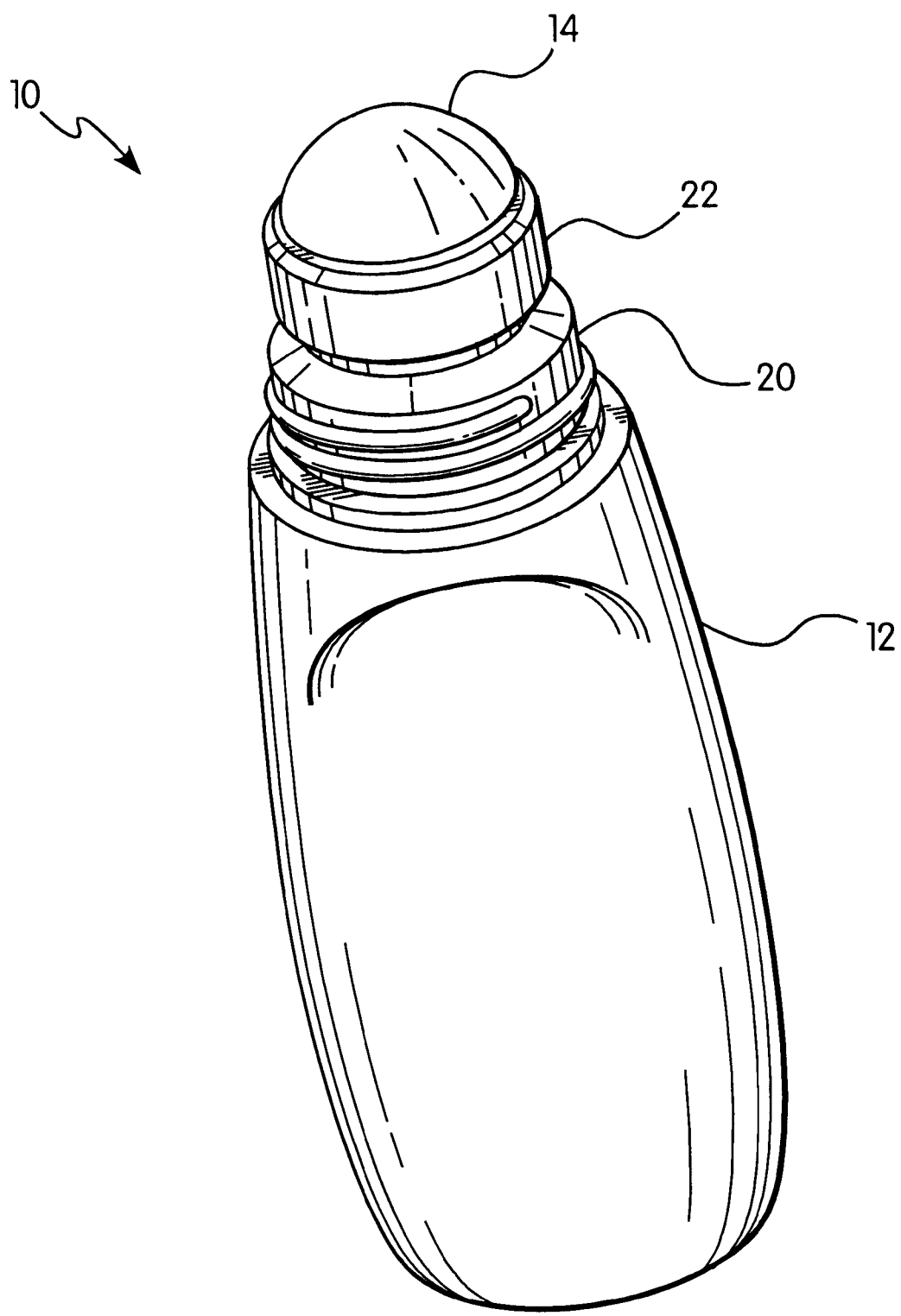
FIG. 1 shows a perspective view of a container with an applicator ball in accordance with an exemplary embodiment of the present invention.
Figure 2:
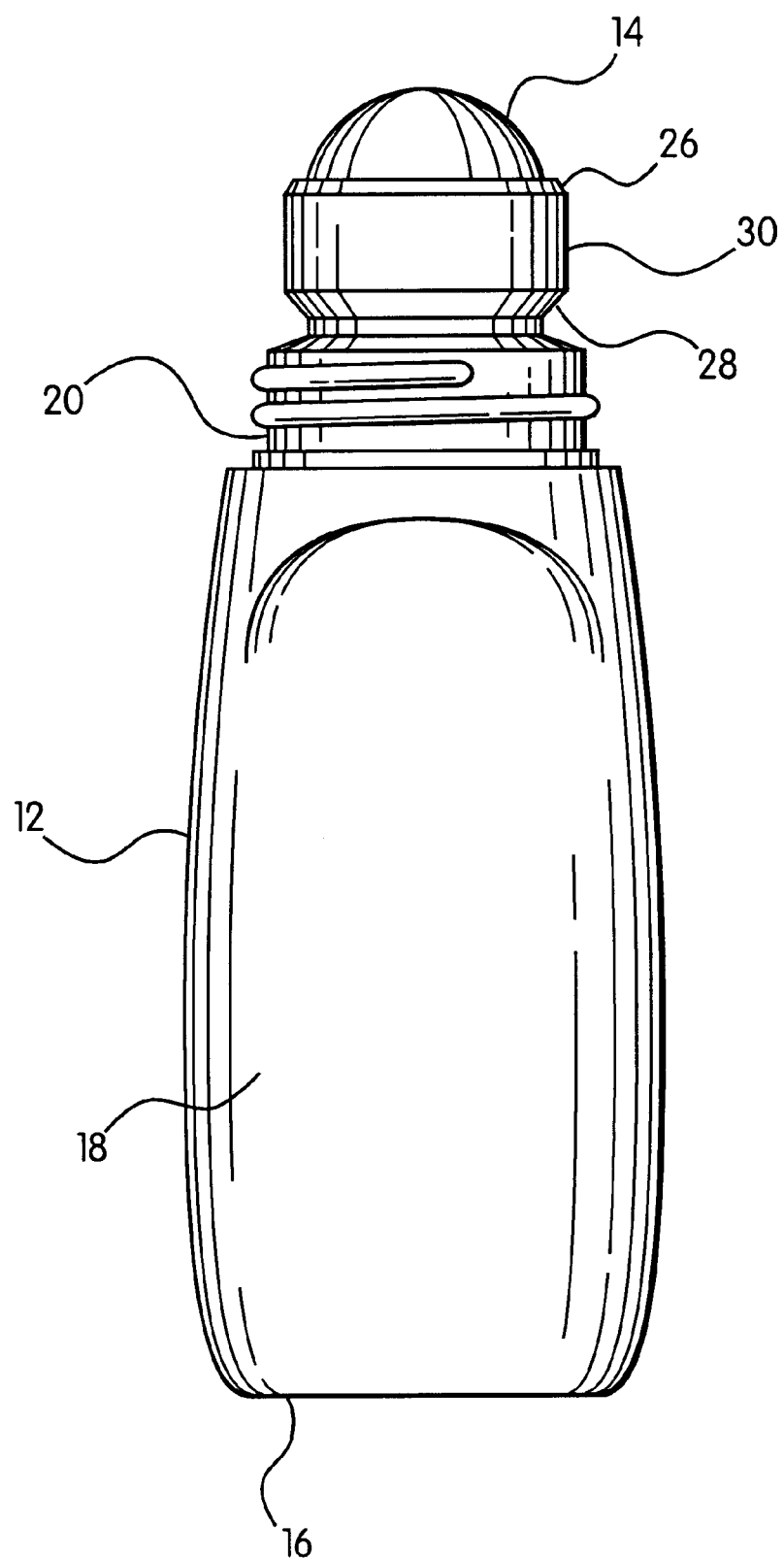
FIG. 2 shows a front view of a container with an applicator ball in accordance with an exemplary embodiment of the present invention.
Figure 3:
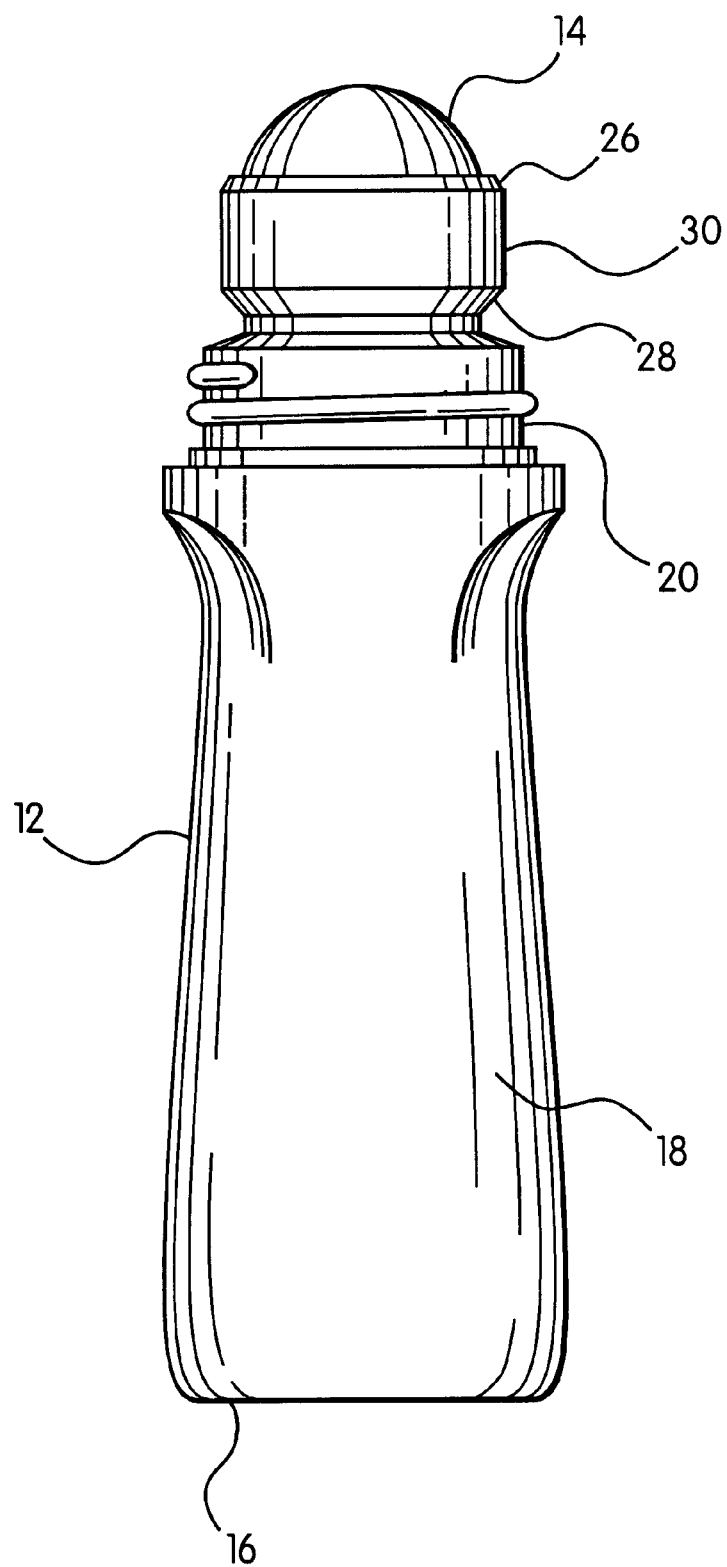
FIG. 3 shows a side view of a container with an applicator ball in accordance with an exemplary embodiment of the present invention.
Figure 4:
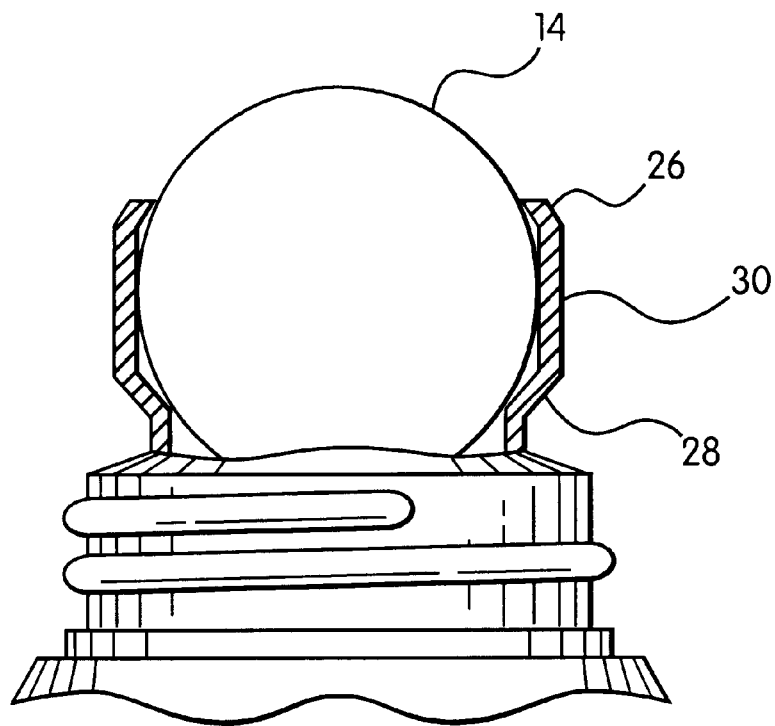
FIG. 4 shows a side view of an applicator ball located within a ball seat in accordance with an exemplary embodiment of the present invention.

FIGS. 1 to 5 show an exemplary embodiment of the present invention. Roll-on applicator 10 includes container 12, collar 20, ball seat 22 and applicator ball 14.

Container 12 serves as a housing to hold the body powder that is to be dispensed. Container 12 can be in the form of any volumetric geometric shape. Container 12 features base 16 and side walls 18. The geometric shape of base 16 defines the volumetric shape of container 12. For example, the shape of base 16 can be any type of geometric shape, for example a rectangle, an ellipse or a circle. Extending from base 16 are side walls 18. Side walls 18 can extend from base 16 in a perpendicular manner such that side walls 18 are transverse to base 16 or side walls 18 can extend from base 16 at an angle. Angling side walls 18 allow container 12 to assume a tapered shape. Side walls 18 can be smooth or ridged, for example to make container 12 ergonomic.

Located opposite of base 16 and connected to the top of container 12 is collar 20. Collar 20 is a circular ring that can be threaded on its outer surface to allow container 12 engage a closure device, for example a screw-on cap or a snap-on lid. For example, a cap can be releasably attached to collar 20 to prevent roll-on applicator from leaking any body powder when stored or in transit. In lieu of container 12, any other type of packaging as known in the art, for example a bottle can be used.

Container 12 and collar 20 can be made of plastic, for example polyethylene, polypropylene, and polyvinyl chloride. Furthermore, the material of container 12 can be pliable or rigid. Also the elements of container 12 can be made as single piece or separate construction.

Figure 5:
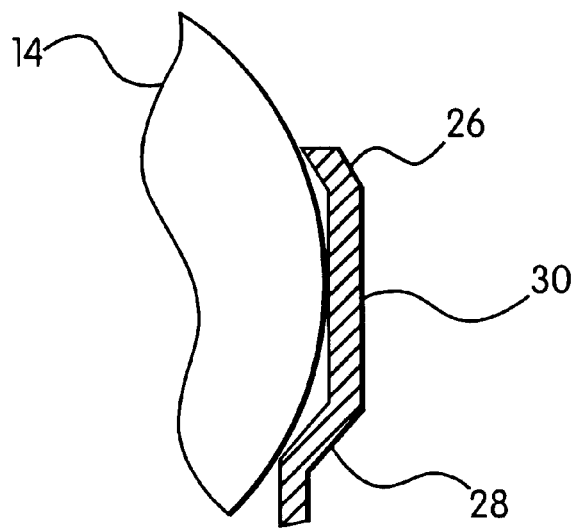
FIG. 5 shows a partial side view of an applicator ball in contact with a ball seat in accordance with an exemplary embodiment of the present invention.

Attached to collar 20 is ball seat 22. The function of ball seat 22 is to allow applicator ball 14 to freely rotate within container 12 and to retain applicator ball 14 within container 12. Any means known to one skilled in the art can be implemented to design a ball seat 22 to retain applicator ball 14 in container 12 and/or collar 20. For example, ball seat 22 as shown in FIG. 5 has top end 26, bottom end 28 and wall 30. Ball seat 22 should be of a geometric shape that corresponds to the shape of applicator ball 14. For example, if applicator ball 14 is a sphere, then ball seat 22 takes the shape of a circular ring. Thus, in this example, top end 26, bottom end 28 and wall 30 are all rings. In order to prevent applicator ball 14 from falling out of container 12, top end 26 has a diameter that is smaller than the diameter of applicator ball 14. The diameter of bottom end 28 is also smaller than the diameter of applicator ball 14 to prevent applicator ball 14 from falling into container 12 if both container 12 and collar 20 are sized to each have a diameter greater than applicator ball 14. The diameter of wall 30 is sized such that applicator ball 14 can freely rotate within ball seat 22.

Ball seat 22 is made of a material identical to or compatible with the materials used to make container 12 and/or collar 20. As with collar 20, ball seat 22 in combination with container 12 and collar 20 can be of a single unitary construction or separate parts.

Applicator ball 14 is preferably a round ball, but it can also be elliptical or cylindrical or any other shape that allows it to rotate with respect to container 12. The surface of applicator ball 14 can be smooth or textured. For example, the surface can have grooves or hair-like projections that help the dispersion of the baby powder onto skin. The diameter of the ball can range from about 1.2 cm to about 4 cm.

Contained within the roll-on applicator 10 is a body powder that is suitable for topical application on the skin, for example a baby powder composition. Preferably, the body powder is not a liquid. The body powder is also preferably anhydrous. The baby powder is composed of at least an absorbent powder and a flow agent.

Any type of particulate solid that is able to absorb moisture or wetness and safe for use on baby skin is suitable for use as the absorbent powder. Examples of absorbent powders include, but are not limited to, talc, potato starch, oat starch, tapioca starch, legume starch, soy starch, turnip starch, corn starch, rice starch, aluminum starch octenyl succinate, kaolin, microcrystalline cellulose, calcium silicate, amorphous silicas, calcium carbonate, magnesium carbonate, zinc carbonate and mixtures thereof. Corn starch is a preferred absorbent powder. The concentration of the absorbent powder in the baby powder can range from about 95% to about 99% by weight of the baby powder composition. The particle sizes of the absorbent powder is preferably less than or equal to about seventy-five microns.

In addition to the absorbent powder, the baby powder includes a flow agent. The flow agent increase the flowability or prevents caking of the absorbent powder. A preferred flow agent in th resent invention is tricalcium phosphate. Other examples of flow agents can be found in *McCutcheon's Functional Materials*, 1992 Edition, Vol. 2, pp. 11–12, incorporated herein by reference. Examples of flow agents include, but are not limited to tricalcium phosphate, calcium carbonate, silica, calcium silicate, mica and kaolin. The concentration of the flow agent in the baby powder can range from about 0.1% to about 1%, preferably from 0.2% to about 0.5%.

In addition to the absorbent powder and flow agent, the baby powder can include other ingredients appropriate for topical use. Examples of categories of optional ingredients include, but are not limited to, odor control agents, anti-microbial agents, anti-fungal agents, skin protectants, emollients, moisturizers, anti-oxidants, binders and anti-pruritic agents, fragrances, colorants and preservatives.

Examples of odor control agents include, but are not limited to, sodium carbonate, charcoal and mixtures thereof. The odor control agent can range in a concentration from about 0.1% to about 50% by weight of the baby powder composition.

Examples of anti-microbial and anti-fungal agents include, but are not limited to, zinc phenolsulfonate, zinc oxide, zinc riconoleate, zinc undecylenate, triclosan and mixtures thereof. The anti-microbial and/or antifungal agents can range from about 0.1% to about 10% by weight of the baby powder composition.

Examples of skin protectants include, but are not limited to, corn starch, kaolin, mineral oil, dimethicone, colloidal oatmeal, zinc oxide and mixtures thereof. The skin protectants can range from about 0.1% to about 10% by weight of the baby powder composition.

Examples of emollients and moisturizers include, but are not limited to, tocopheryl acetate, tocopherol, retinol, retinyl acetate, retinyl palmitate, aloe, vegetable oils, mineral oil, glycerin, propylene glycol, petrolatum, ascorbyl palmitate, sodium ascorbate, jojoba oil, and mixtures thereof. The emollients and/or moisturizers can range from about 0.1% to about 25% by weight of the baby powder composition. Also included within the class of emollients and moisturizers are stearates and/or fatty acid derivatives. Examples of fatty acid esters include, but are not limited to, palmitates, oleates, laurates, linoleates, myristates and butyrates. In addition to emollients and moisturizers, other skin feel agents such as nylon, polyethylene and polytetrafluroethylene can be incorporated in the baby powder.

Examples of anti-oxidants include, but are not limited to, retinol, retinyl almitate, retinyl acetate, ascorbyl palmitate, sodium ascorbate, tocopherol, tocopheryl cetate and mixtures thereof. The anti-oxidants can range from about 0.1% to about 10%, by weight of the baby powder composition.

Binders are substances that help the baby powder to adhere to skin. Examples of binders include, but are not limited to calcium stearate, zinc stearate, magnesium stearate, dimethicone and mixtures thereof. The binders can range from about 0.1% to about 15% by weight of the baby powder composition.

Examples of anti-pruritics include, but are not limited to hydrocortisone, hydrocortisone acetate, colloidal oatmeal, magnesium-L-lactate and mixtures thereof. The anti-pruritics can range from about 0.1% to about 20% by weight of the baby powder composition.

Colorants, fragrances and/or preservatives can be optionally added to the baby powder composition.

EXAMPLE

Set forth below in the table is an example of a non-liquid and anhydrous baby powder composition that is suitable for use in the roll-on applicator.

| Ingredient | Function | % (w/w) |
| --- | --- | --- |
| corn starch | absorbent powder | 98.00% |
| tricalcium phosphate | flow agent | 0.25% |
| diazolidinyl urea | preservative | 0.20% |
| methyl paraben | preservative | 0.15% |
| propyl paraben | preservative | 0.15% |

The baby powders of the present invention are prepared by blending the absorbent powder and flow agents in any suitable mixer, for example a vee-blender, a double cone blender, or ribbon blender until the mixture is uniform. Any optional ingredients can also be added to the mixture of absorbent powder and flow agents while they are being blended to form a mixture.

Once the baby powder is uniformly blended, the baby powder can filled into the containers of the roll-on applicator. The applicator ball is subsequently attached to the container. The roll-on applicator can then be used to topically apply the baby powder to skin, especially occluded skin in the diaper area of a baby that is prone to diaper rash, or other condition resulting from hyperhydration of the skin, for example, heat rash, abrasion, pressure marks and skin barrier loss. To apply the powder, the roll-on applicator with baby powder is inverted and rolled across the skin. As the applicator rolls, baby powder flows from the container and onto the ball. The roll-on applicator gives the user more control as to where the body powder is applied and minimized any creation of powder clouds.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed:

1. A roll-on applicator for dispensing baby powder comprising:
    a container containing a baby powder composition;
    a collar connected to said container;
    a ball seat connected to said collar; and
    an applicator ball rotatably attached to said ball seat;
    wherein said baby powder composition is non-liquid and comprises an absorbent powder and a flow agent;
    wherein said baby powder composition comprises corn starch and tricalcium phosphate; and wherein said baby powder composition comprises from about 0.1% to about 1% by weight of said tricalcium phosphate.

2. The roll-on applicator for dispensing baby powder of claim 1, wherein said absorbent powder is selected from the group consisting of talc, potato starch, oat starch, tapioca starch, legume starch, soy starch, turnip starch, corn starch, rice starch, aluminum starch octenyl succinate, kaolin, microcrystalline cellulose, calcium silicate, amorphous silicas, calcium carbonate, magnesium carbonate, zinc carbonate and mixtures thereof.

3. The roll-on applicator for dispensing baby powder of claim 1, wherein said flow agent is selected from the group consisting of tricalcium phosphate, calcium carbonate, silica, calcium silicate, mica and kaolin.

4. The roll-on applicator for dispensing baby powder of claim 1, wherein said baby powder composition comprises from about 0.2% to about 0.5% by weight of said tricalcium phosphate.

5. The roll-on applicator for dispensing baby powder of claim 4, wherein said baby powder composition comprises from about 95% to about 99% by weight of said corn starch.

6. The roll-on applicator for dispensing baby powder of claim 1, wherein said applicator ball has a textured surface.

7. The roll-on applicator for dispensing baby powder of claim 1, wherein said container, said collar and said ball seat are of a unitary construction.

8. The roll-on applicator of claim 1, wherein said absorbent powder comprises particles having particle sizes less than or equal to seventy-five microns.

9. A method of applying body powder to skin comprising the step of
    dispensing a non-liquid baby powder composition from a roll-on applicator across said skin;
    wherein said baby powder composition comprises an absorbent powder and a flow agent and wherein said roll-on applicator comprises a container, a collar, a ball seat and an applicator ball;
    wherein said baby powder composition comprises corn starch and tricalcium phosphate; and wherein said baby powder composition comprises from about 0.1% to about 1% by weight of said tricalcium phosphate.

10. The method of claim 9, wherein said absorbent powder is selected from the group consisting of talc, potato starch, oat starch, tapioca starch, legume starch, soy starch, turnip starch, corn starch, rice starch, aluminum starch octenyl succinate, kaolin, microcrystalline cellulose, calcium silicate, amorphous silicas, calcium carbonate, magnesium carbonate, zinc carbonate and mixtures thereof.

11. The method of claim 9, wherein said flow agent is selected from the group consisting of tricalcium phosphate, calcium carbonate, silica, calcium silicate, mica and kaolin.

12. The method of claim 11, wherein said baby powder composition comprises from about 0.2% to about 0.5% by weight of said tricalcium phosphate.

13. The method of claim 12, wherein said baby powder composition comprises from about 95% to about 99% by weight of said corn starch.

14. The method of claim 9, wherein said skin is an infant's diaper area.

15. The method of claim 9, wherein said absorbent powder comprises particles having particle sizes less than or equal to seventy-five microns.

* * * * *